US012778140B2

(12) United States Patent
Kito et al.

(10) Patent No.: US 12,778,140 B2
(45) **Date of Patent: *Nov. 3, 2026**

(54) PLANT STOMATA OPENING PROMOTING AGENT

(71) Applicant: OAT Agrio Co., Ltd., Tokyo (JP)

(72) Inventors: Keijiro Kito, Naruto (JP); Sumio Iwai, Kagoshima (JP); Michio Onjo, Kagoshima (JP)

(73) Assignee: OAT AGRIO CO., LTD., Tokyo (JP)

( * ) Notice: Subject to any disclaimer, the term of this patent is extended or adjusted under 35 U.S.C. 154(b) by 565 days.

This patent is subject to a terminal disclaimer.

(21) Appl. No.: 17/783,399

(22) PCT Filed: Dec. 25, 2020

(86) PCT No.: PCT/JP2020/048949

§ 371 (c)(1),
(2) Date: Jun. 8, 2022

(87) PCT Pub. No.: WO2021/132641

PCT Pub. Date: Jul. 1, 2021

(65) Prior Publication Data

US 2023/0034248 A1 Feb. 2, 2023

(30) Foreign Application Priority Data

Dec. 28, 2019 (JP) ................................ 2019-239993

(51) Int. Cl.
*A01N 65/12* (2009.01)
*C07H 15/256* (2006.01)

(52) U.S. Cl.
CPC ........... *A01N 65/12* (2013.01); *C07H 15/256* (2013.01)

(58) Field of Classification Search
CPC .................................................. C07H 15/256
See application file for complete search history.

(56) References Cited

U.S. PATENT DOCUMENTS

| | | | | |
|---|---|---|---|---|
| 4,931,083 A * | 6/1990 | Beck | A01N 43/653 504/225 |
| 2011/0038957 A1* | 2/2011 | Fowler | A23L 27/36 424/725 |
| 2017/0311598 A1* | 11/2017 | Nonomura | A01N 63/50 |
| 2024/0225012 A1* | 7/2024 | Kito | A01P 21/00 |

FOREIGN PATENT DOCUMENTS

| | | | |
|---|---|---|---|
| CN | 1394831 | | 2/2003 |
| CN | 102146000 | | 8/2011 |
| JP | 10194908 A | * | 7/1998 |
| JP | 2003261398 A | * | 9/2003 |
| JP | 2016-117685 | | 6/2016 |
| JP | 2021-107375 | | 7/2021 |

OTHER PUBLICATIONS

International Search Report (ISR) issued Mar. 9, 2021 in International (PCT) Application No. PCT/JP2020/048949.
Saroj K. Sah et al., "Abscisic Acid and Abiotic Stress Tolerance in Crop Plants", Frontiers in Plant Science, vol. 7, Article 571, pp. 1-26, May 2016.
S. Xu, et al., "Effect of foliar application of stevioside on growth and quality of cherry tomato", Beifang Yuanyi, No. 18, pp. 48-51, p. 48, Section "1.2.1", Fig. 3, 2015, with partial machine translation, cited in ISR.
Keiko Hirata, et al., "Analysis of Stevia Glycosides in Stevia Products of Natural Sweetening and Evaluation of their Chemical Quality", Annual Report of the Tokyo Metropolitan Research Laboratory of Public Health, vol. 53, pp. 108-112, p. 108, left column, lines 1-10, Table 1, 2002, with partial machine translation, cited in ISR.
Brás Heleno de Oliveira et al., "Plant growth regulation activity of steviol and derivatives", Science Direct Phytochemistry, vol. 69, pp. 1528-1533, 2008.
Office Action issued Mar. 16, 2020 in corresponding Japanese Patent Application No. 2019-239993, with machine translation.
Extended European Search Report issued Nov. 24, 2023 in corresponding European Patent Application No. 20908038.1, 6 pages.
Anonymous: "Stevia—Wikipedia", Sep. 25, 2019 (Sep. 25, 2019), pp. 1-11, XP093100368, Retrieved from the Internet: Nov. 10, 2023, 11 pages.
Nguyen et al., "Enzymatic Production of Steviol Glucosides Using [beta]-Glucosidase and Their Applications" Enzymes in Food Biotechnology, 2018, Elsevier, XP093100463, ISBN: 978-0-12-813280-7, pp. 405-418, DOI: 10.1016/B978-0-12-813280-7.00023-2.
Eun et al., "Stomatal opening by fusicoccin is accompanied by depolymerization of actin filaments in guard cells", PLANTA, 2000, vol. 210, pp. 1014-1017, XP093101968, DOI: 10.1007/s004250050711.
International Preliminary Report on Patentability issued Aug. 11, 2021 in International (PCT) Application No. PCT/JP2020/048949.

* cited by examiner

*Primary Examiner* — Gina C Justice
(74) *Attorney, Agent, or Firm* — Wenderoth, Lind & Ponack, L.L.P.

(57) ABSTRACT

It is an object of the present invention to provide a plant stomatal opening promoting agent that is inexpensive, highly safe, and has an excellent stomatal opening promoting effect. The present invention is a plant stomatal opening promoting agent comprising stevia.

2 Claims, 16 Drawing Sheets

PLANT STOMATA OPENING PROMOTING AGENT

TECHNICAL FIELD

The present invention relates to a plant stomatal opening promoting agent.

BACKGROUND ART

The stomata found in the epidermis of terrestrial plants are composed of a pair of guard cells, which control their aperture to thereby control the flow of photosynthesis-related substances (such as carbon dioxide, oxygen, and water) in and out of the plants, between the plants and the atmosphere.

It is known that the stomata open under sunlight (during daytime) in which the plants actively photosynthesize, particularly in response to light in the blue light range that acts as a signal, and promote the uptake of carbon dioxide required for photosynthesis, transpiration, the release of oxygen, and the like.

Transpiration lowers the leaf temperature raised by strong sunlight, and simultaneously promotes the uptake of water and inorganic nutrients in roots. Conversely, when plants are exposed to drought stress, the stomata close in response to a plant hormone (abscisic acid) produced in response to the drought stress, and prevent water loss from the plant body. On the other hand, the function of the stomata suppresses the uptake of carbon dioxide, transpiration, the release of oxygen, and the like (Non Patent Literature 1). Thus, artificial promotion of stomatal opening can be expected to lead to effects such as improving the heat stress resistance, promoting the absorption of fertilizer components through leaves, and promoting the emission of harmful gases produced in the plant body. Therefore, stomatal opening promoting substances have been explored in the past.

For example, Patent Literature 1 discloses a plant stomatal opening regulator containing a specific compound such as temsirolimus, known as an anticancer agent. However, temsirolimus is one of the macrolide compounds derived from rapamycin produced by the microorganism *Streptomyces hygroscopicus*, and is expensive for use in plants.

Accordingly, there is an earnest desire for a substance that is inexpensive, highly safe, and has an excellent stomatal opening promoting effect.

CITATION LIST

Patent Literature

Patent Literature 1: JP 2016-117685 A

Non Patent Literature

Non Patent Literature 1: *Frontiers in Plant Science*, May 2016, Volume 7, Article 571, p. 1-26

SUMMARY OF INVENTION

Technical Problem

It is an object of the present invention to provide a plant stomatal opening promoting agent that is inexpensive, highly safe, and has an excellent stomatal opening promoting effect.

Solution to Problem

As a result of extensive research in view of the foregoing object, the inventors of the present invention have found that a sweetening component contained in stevia, which is a raw material of sweeteners, and its analogous compounds have a plant stomatal opening promoting effect. The inventors have also found that the stomatal opening promoting action of these compounds inhibits stomatal closure induction by the stomatal closure-inducing plant hormone, abscisic acid, inhibits the stomatal closure induction in a dark place, and promotes stomatal opening in a bright place. The present invention has been completed as a result of further research based on these findings.

In summary, the present invention is as set forth below.

Item 1.

A plant stomatal opening promoting agent comprising stevia.

Item 2.

The plant stomatal opening promoting agent according to item 1, wherein the promoting agent has abscisic acid-induced stomatal closure inhibitory activity.

Item 3.

The plant stomatal opening promoting agent according to item 1, wherein the promoting agent has stomatal opening promoting activity in a dark place.

Item 4.

The plant stomatal opening promoting agent according to item 1, wherein the promoting agent has stomatal opening promoting activity in a bright place.

Item 5.

The plant stomatal opening promoting agent according to any one of items 1 to 4, wherein the stevia is at least one selected from the group consisting of steviol compounds, stevia extracts, and enzyme-treated stevia.

Item 6.

The plant stomatal opening promoting agent according to any one of items 1 to 5, wherein the stevia is at least one selected from the group consisting of steviol, stevioside, rebaudioside A, rebaudioside B, rebaudioside C, rebaudioside D, rebaudioside E, rebaudioside F, rebaudioside M, steviolbioside, rubusoside, and dulcoside.

Item 7.

The plant stomatal opening promoting agent according to any one of items 1 to 5, wherein the stevia is a stevia extract.

Item 8.

The plant stomatal opening promoting agent according to any one of items 1 to 5, wherein the stevia is enzyme-treated stevia.

Item 9.

The plant stomatal opening promoting agent according to any one of items 1 to 5, wherein the stevia is rebaudioside.

Item 10.

A method of promoting stomatal opening in a plant, using the plant stomatal opening promoting agent according to any one of items 1 to 9 on a plant or in a soil or a culture medium in which the plant is grown.

Item 11.

A method of applying the plant stomatal opening promoting agent according to any one of items 1 to 9 to a plant.

Advantageous Effects of Invention

The present invention can provide a plant stomatal opening promoting agent comprising stevia.

*ghalensis* L., on the stomatal opening promoting activity in a bright place provided by steviol.

Figure 2:
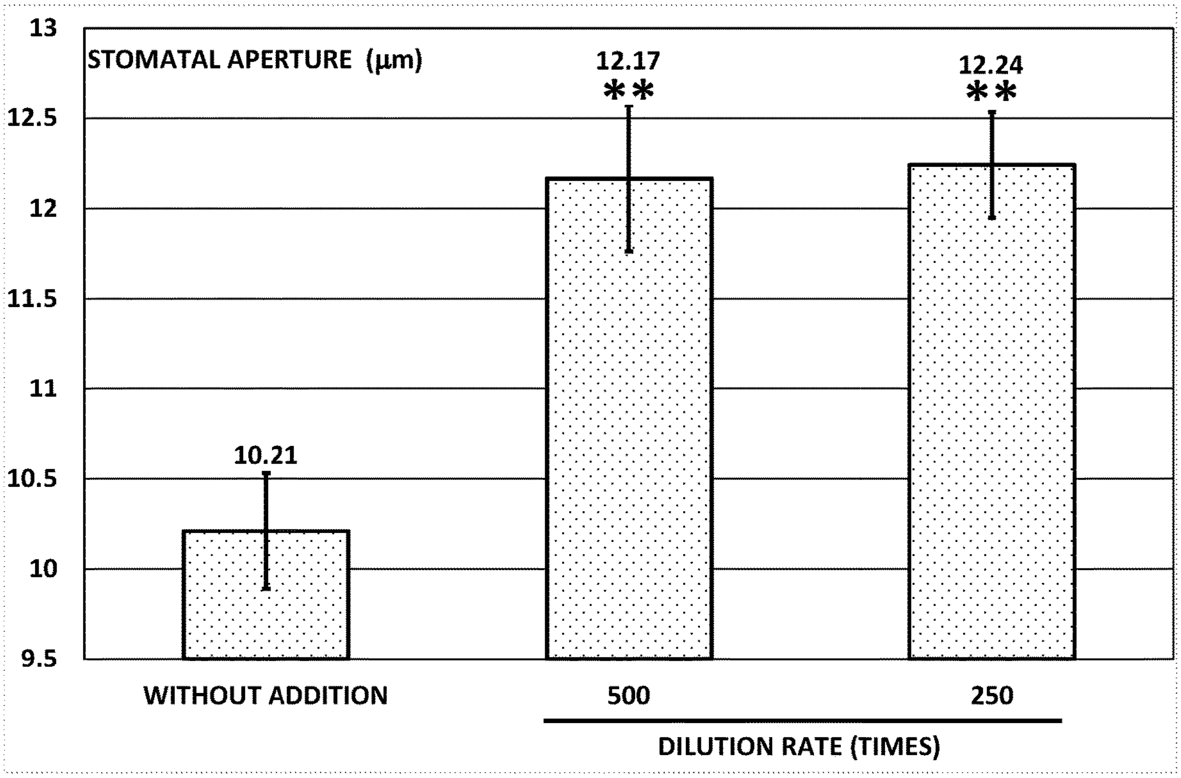

FIG. 2 is a graph showing the results of evaluation performed using the lower epidermis of *Commelina benghalensis* L., on the stomatal opening promoting activity in a bright place provided by FARM A.

Figure 3:
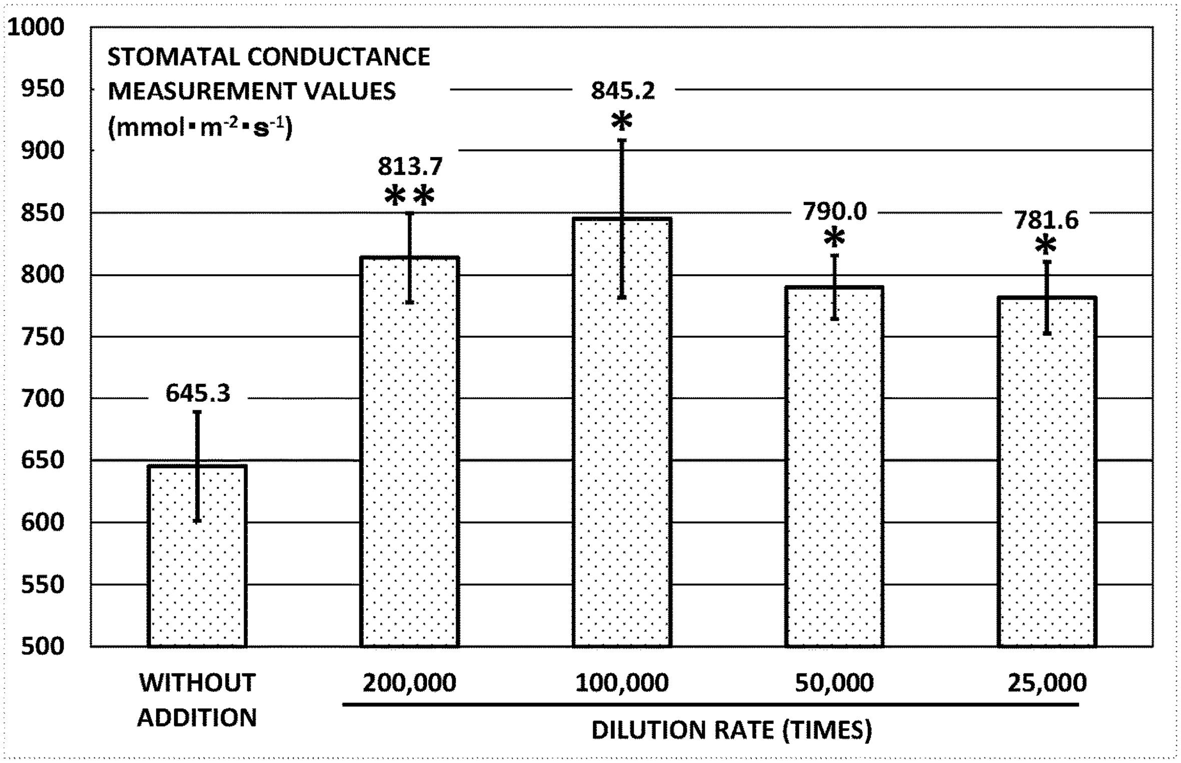

FIG. 3 is a graph showing the results of evaluation performed using potato seedlings, on the stomatal opening promoting activity in a bright place provided by Steviron TK.

Figure 4:
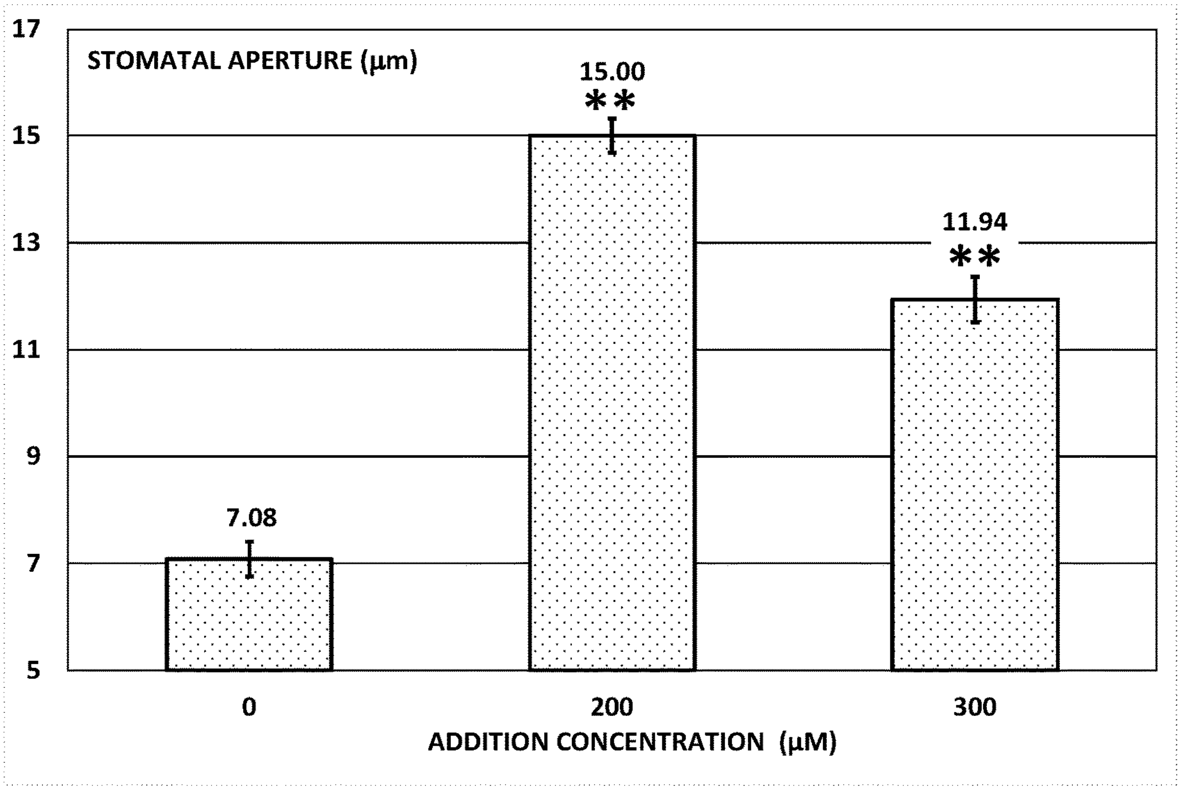

FIG. 4 is a graph showing the results of evaluation performed using the lower epidermis of *Commelina benghalensis* L., on the stomatal opening promoting activity in a dark place provided by steviol.

Figure 5:
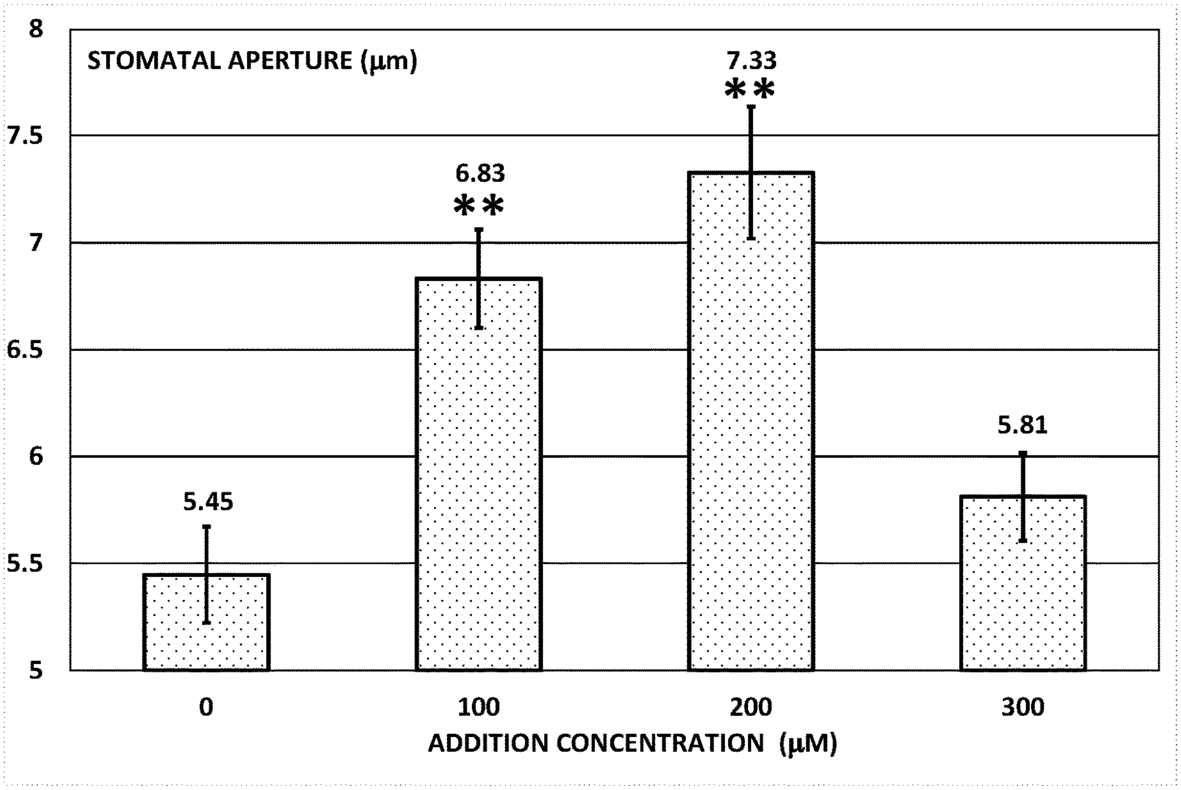

FIG. 5 is a graph showing the results of evaluation performed using the lower epidermis of *Commelina benghalensis* L., on the stomatal opening promoting activity in a dark place provided by stevioside.

Figure 6:
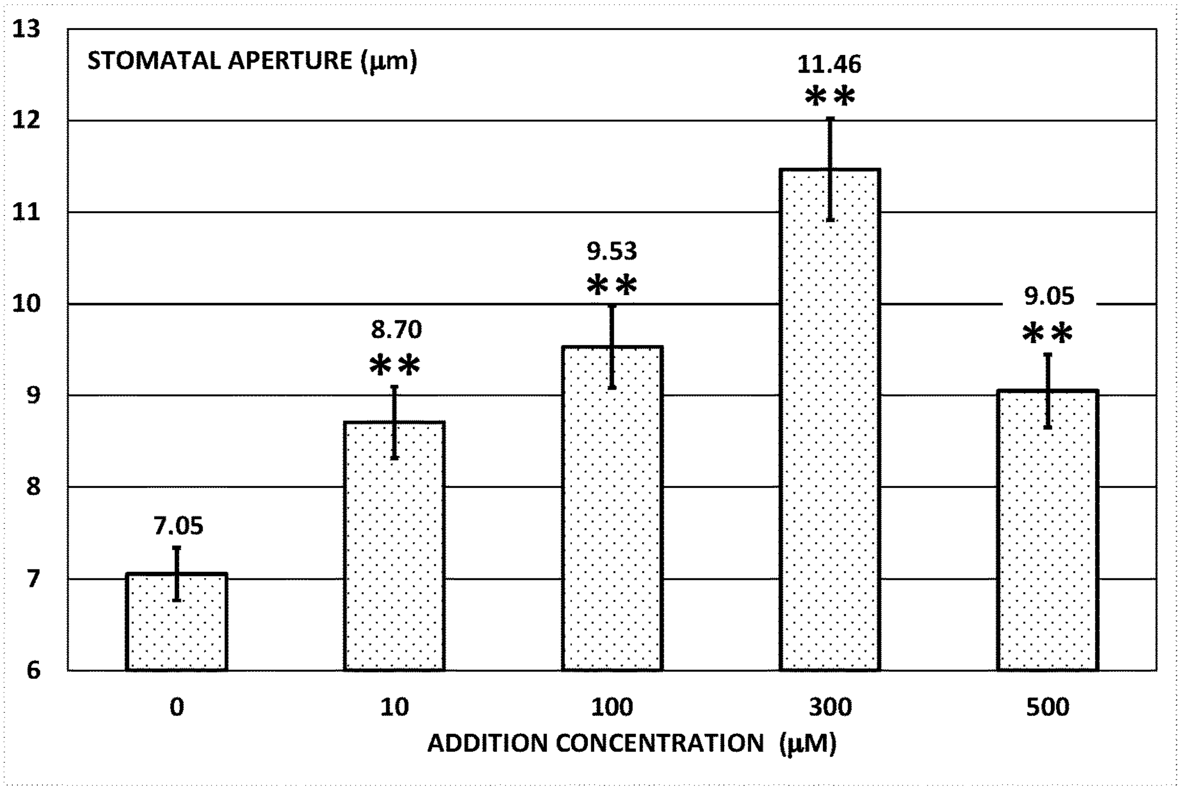

FIG. 6 is a graph showing the results of evaluation performed using the lower epidermis of *Commelina benghalensis* L., on the stomatal opening promoting activity in a dark place provided by rebaudioside A.

Figure 7:
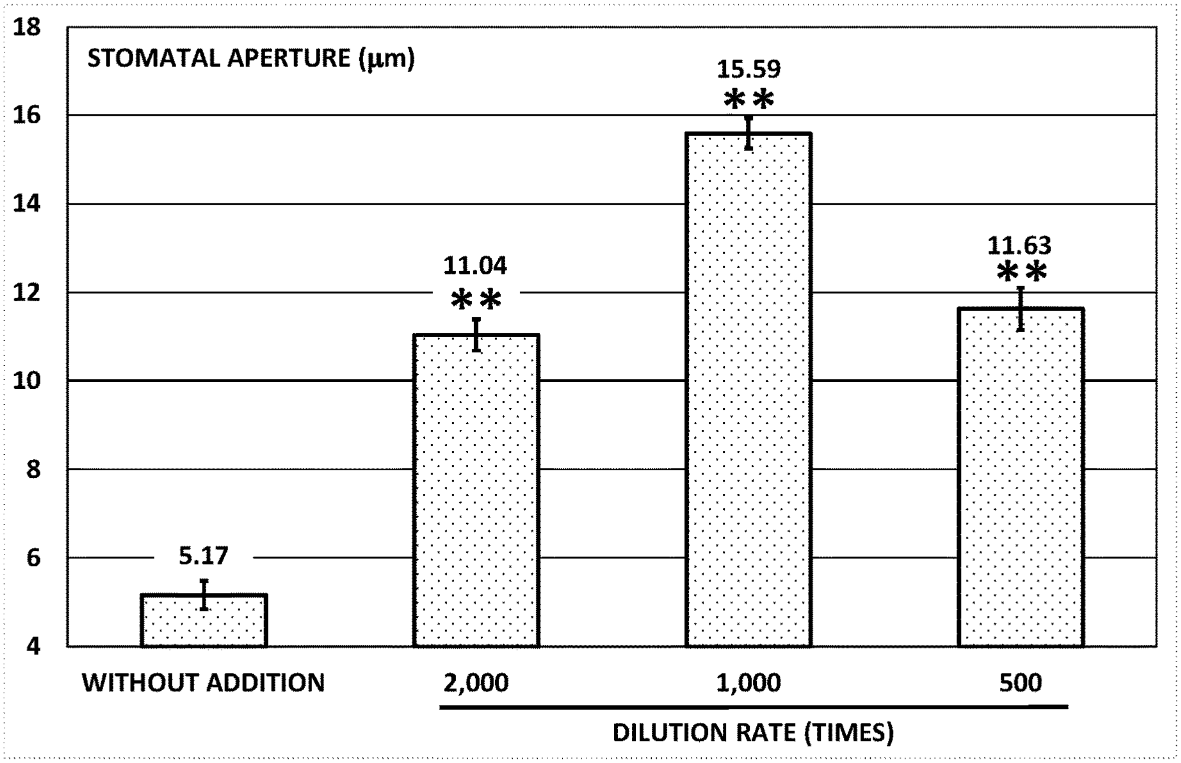

FIG. 7 is a graph showing the results of evaluation performed using the lower epidermis of *Commelina benghalensis* L., on the stomatal opening promoting activity in a dark place provided by FARM A.

Figure 8:
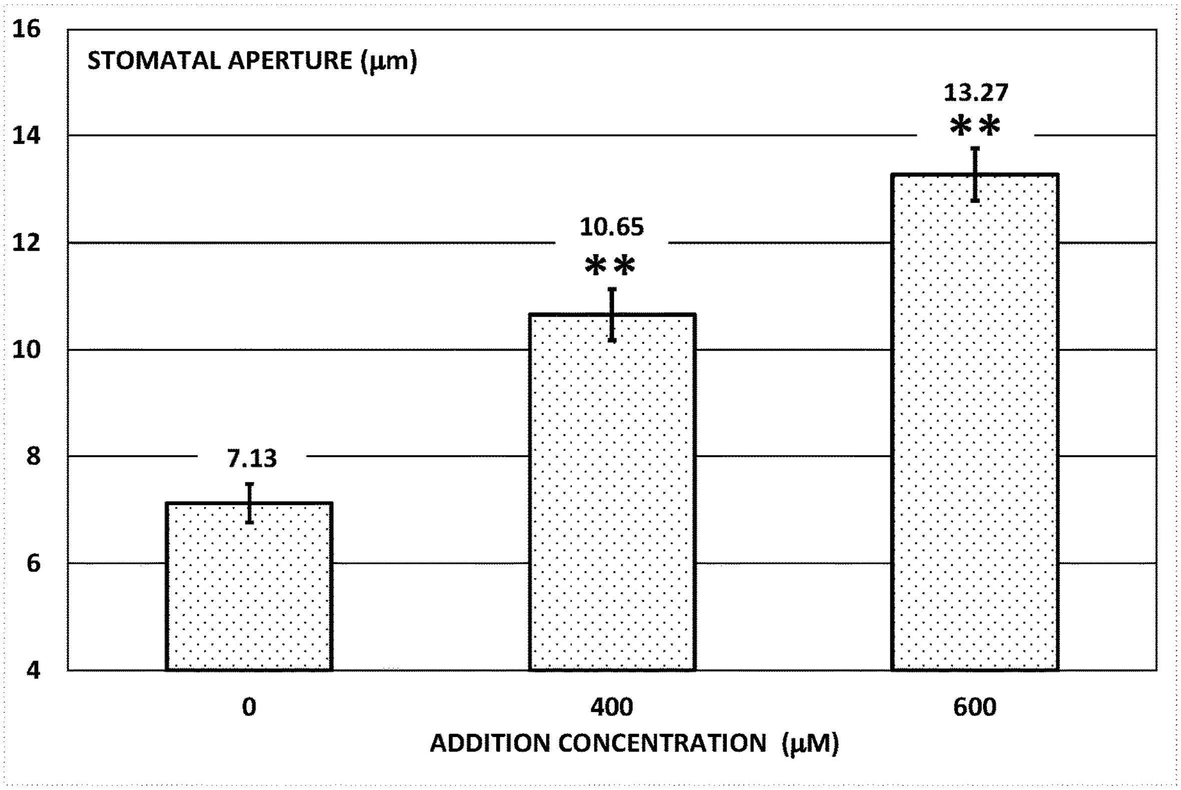

FIG. 8 is a graph showing the results of evaluation performed using the lower epidermis of *Commelina benghalensis* L., on the abscisic acid-induced stomatal closure inhibitory activity provided by steviol.

Figure 9:
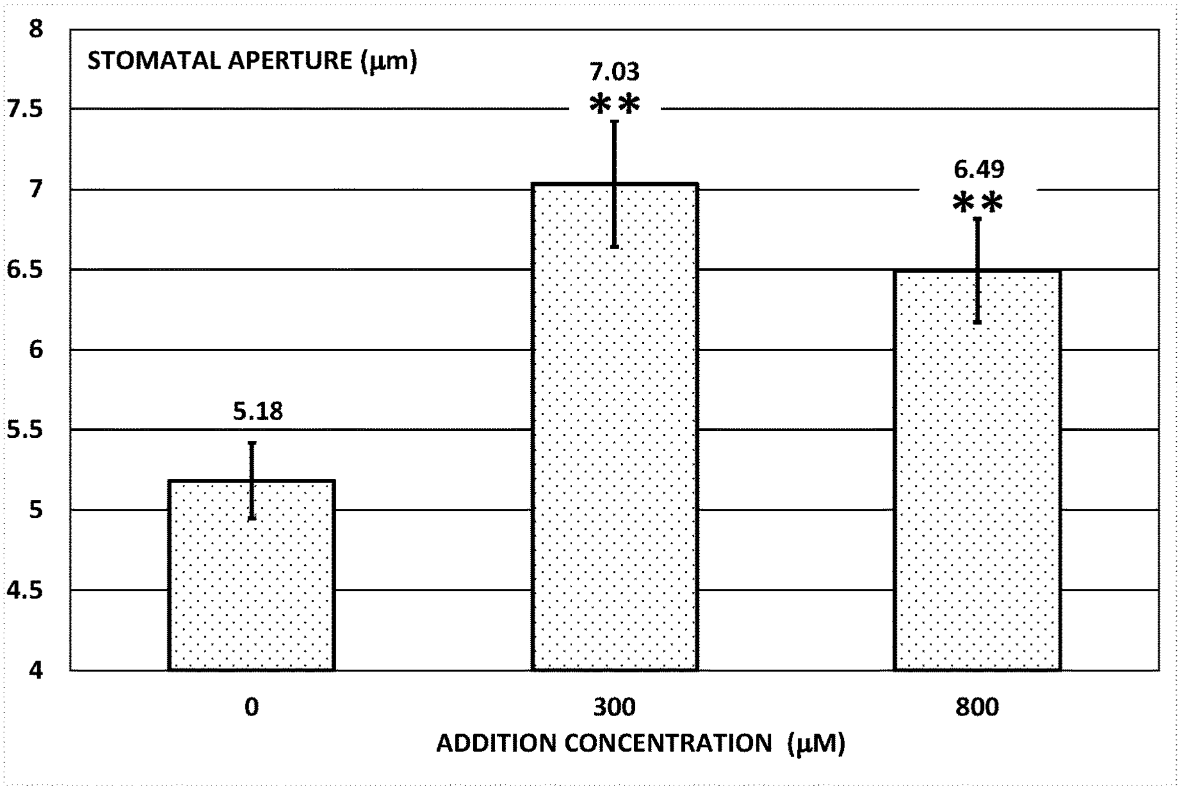

FIG. 9 is a graph showing the results of evaluation performed using the lower epidermis of *Commelina benghalensis* L., on the abscisic acid-induced stomatal closure inhibitory activity provided by stevioside.

Figure 10:
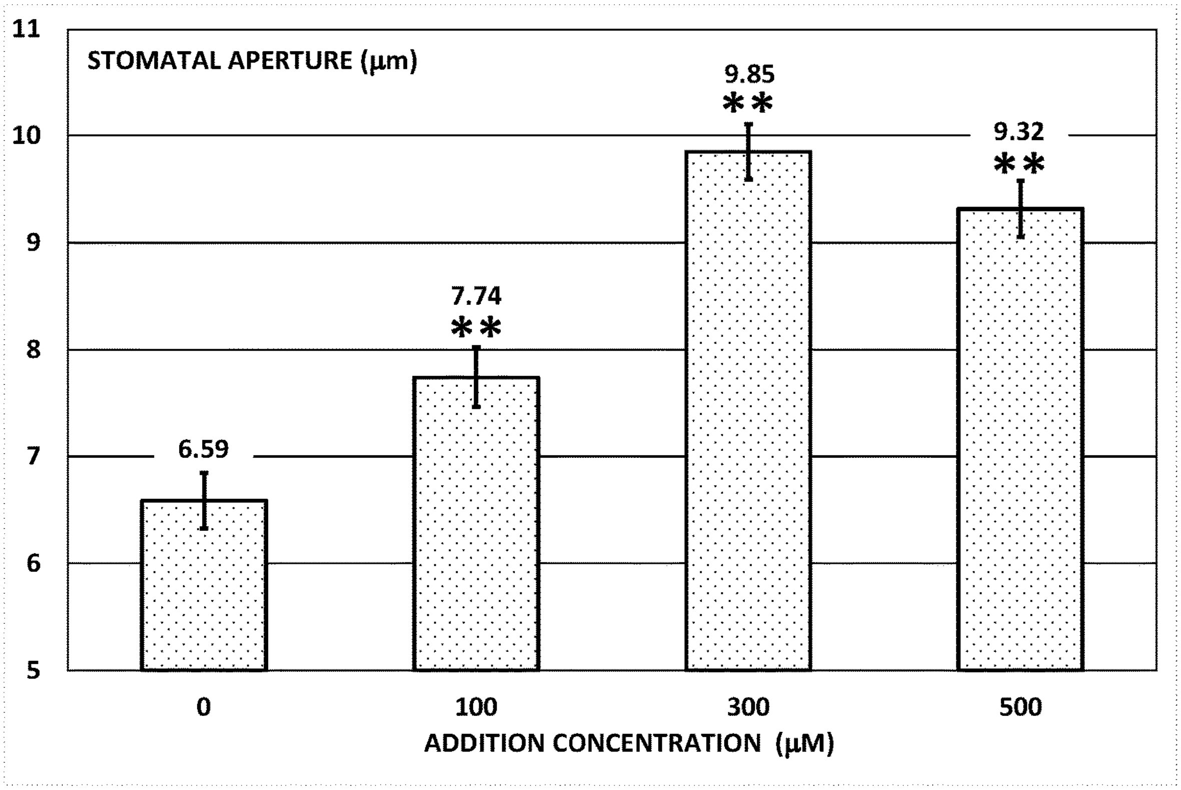

FIG. 10 is a graph showing the results of evaluation performed using the lower epidermis of *Commelina benghalensis* L., on the abscisic acid-induced stomatal closure inhibitory activity provided by rebaudioside A.

Figure 11:
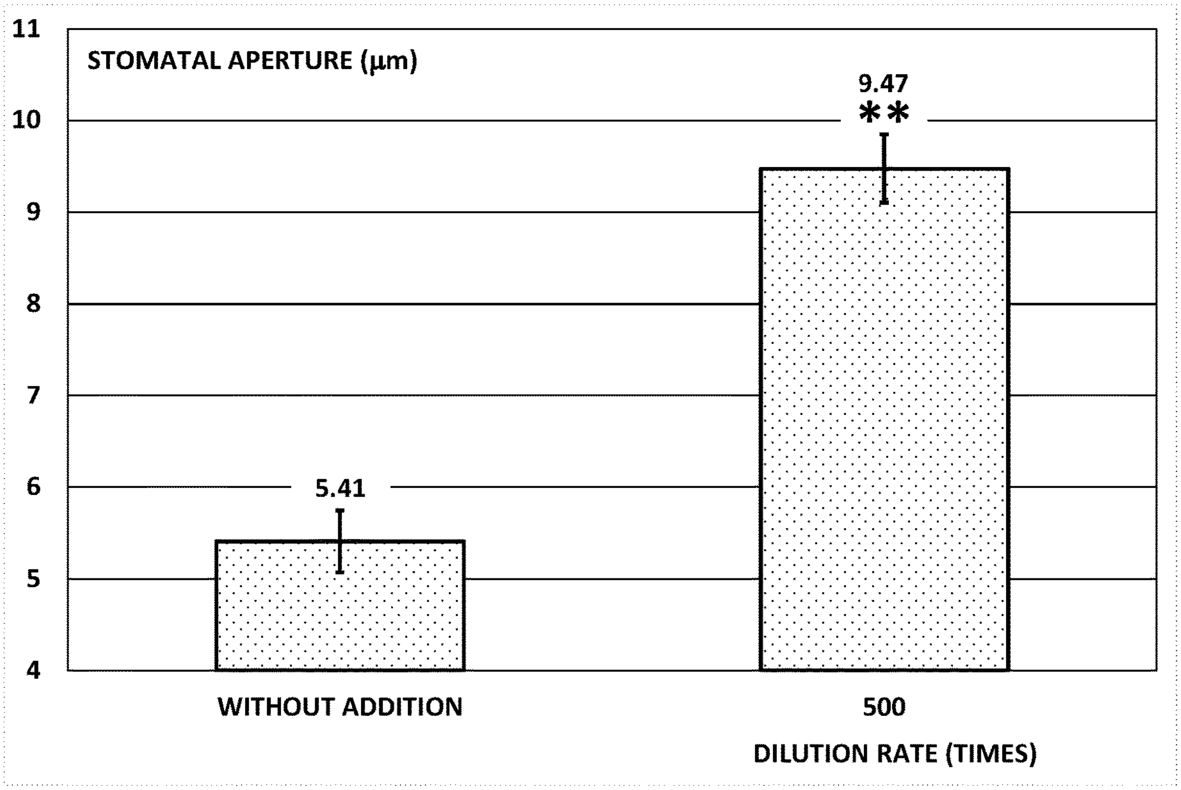

FIG. 11 is a graph showing the results of evaluation performed using the lower epidermis of *Commelina benghalensis* L., on the abscisic acid-induced stomatal closure inhibitory activity provided by FARM A.

Figure 12:
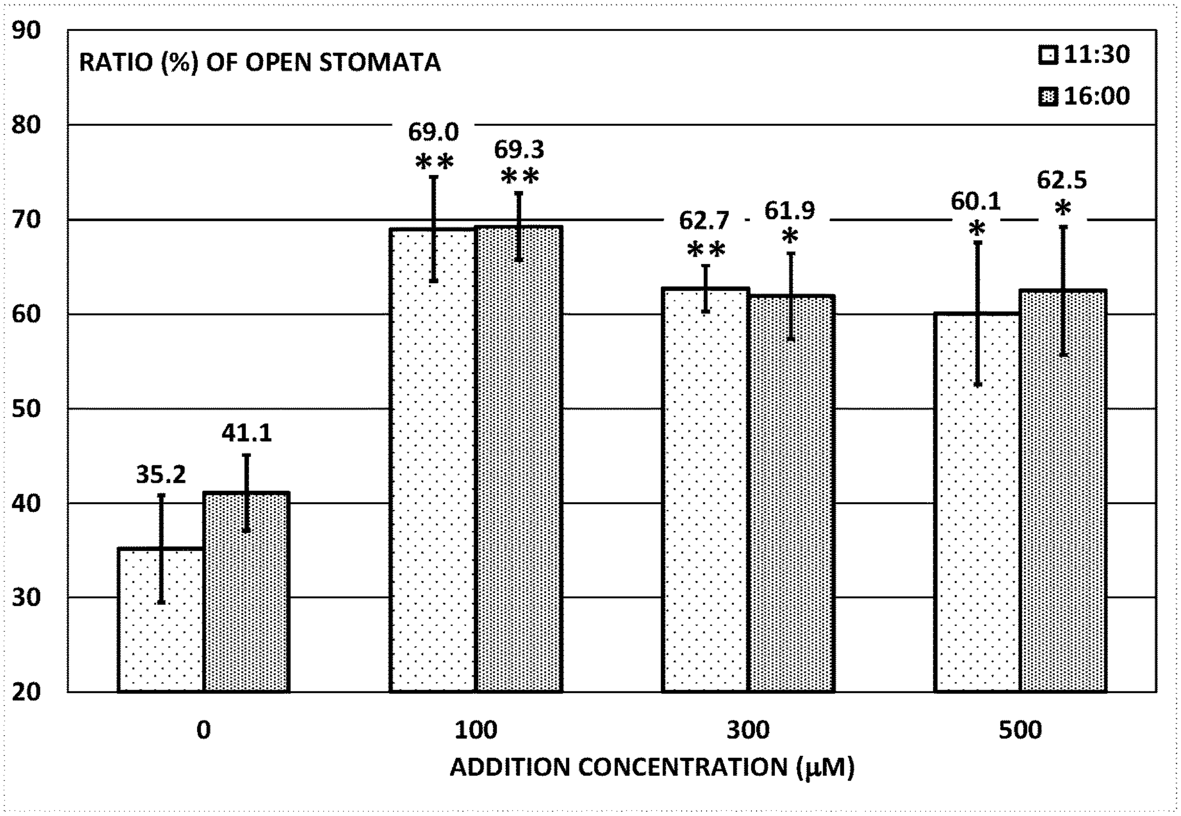

FIG. 12 is a graph showing the results of evaluation performed using tomato seedlings, on the abscisic acid-induced stomatal closure inhibitory activity provided by steviol.

Figure 13:
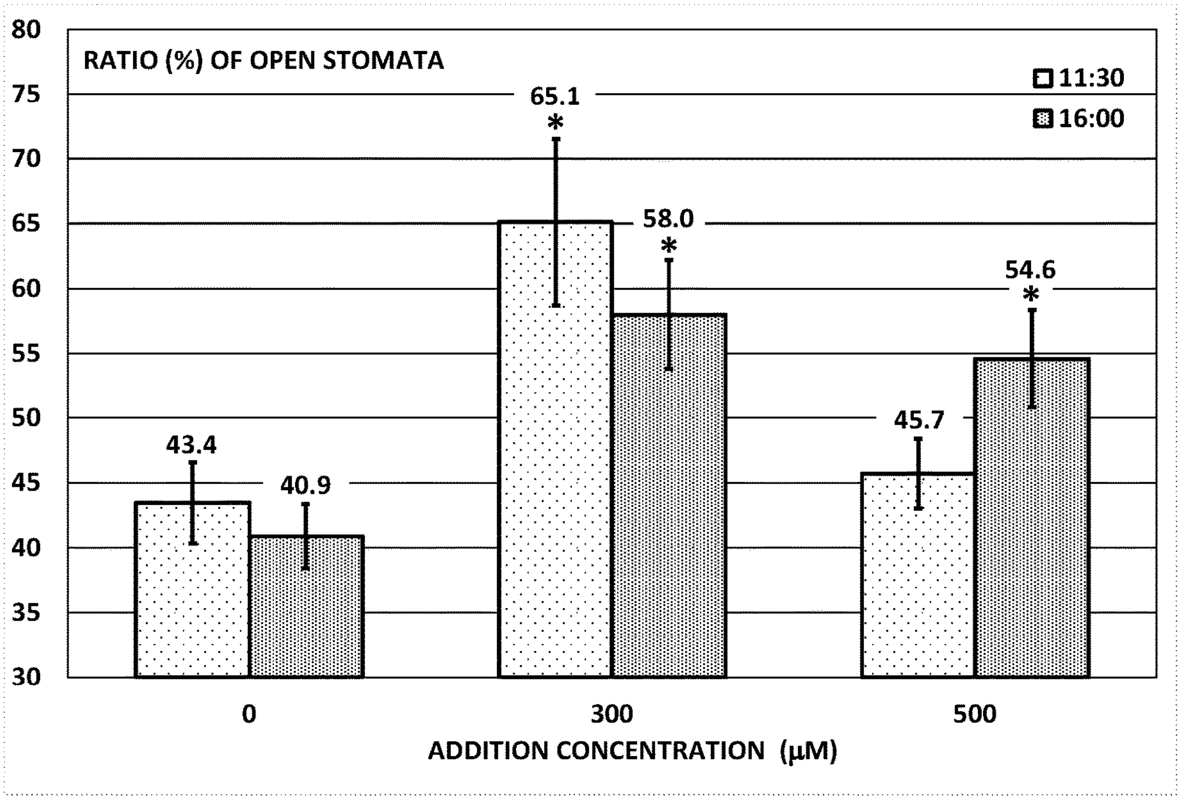

FIG. 13 is a graph showing the results of evaluation performed using tomato seedlings, on the abscisic acid-induced stomatal closure inhibitory activity provided by stevioside.

Figure 14:
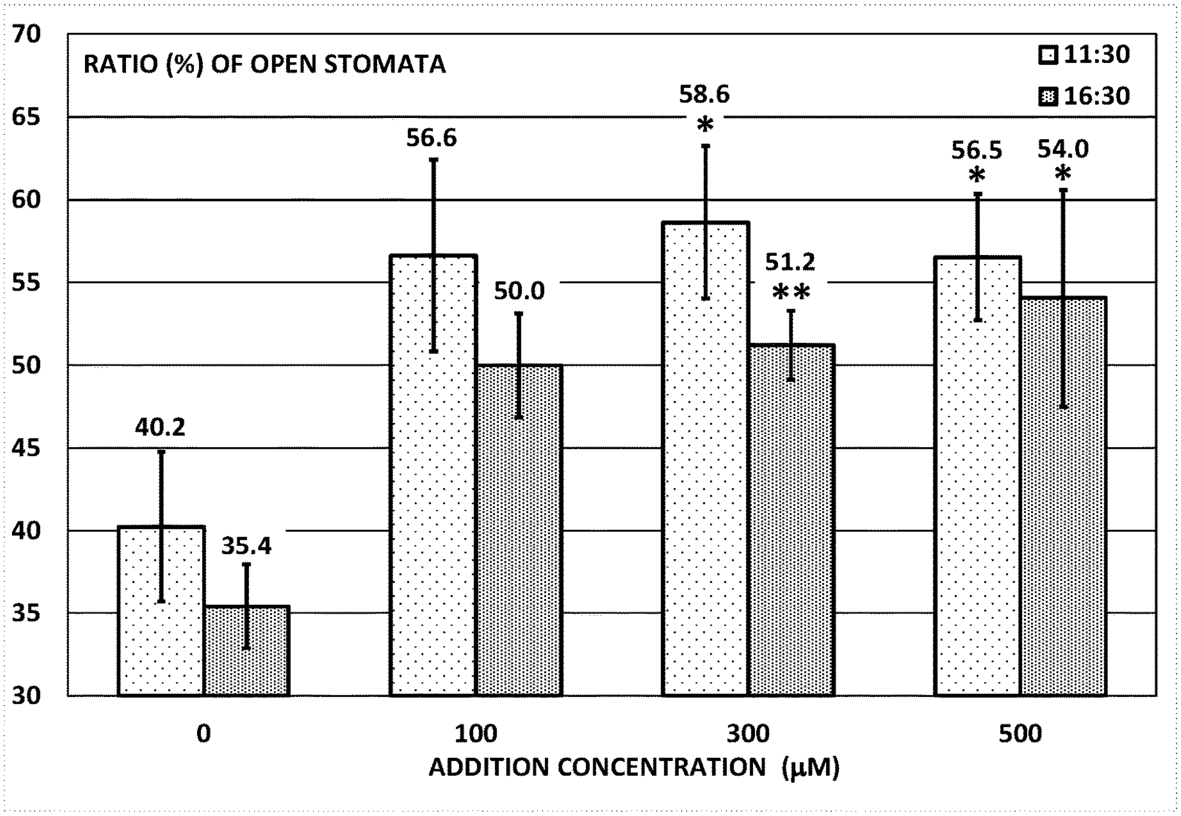

FIG. 14 is a graph showing the results of evaluation performed using tomato seedlings, on the abscisic acid-induced stomatal closure inhibitory activity provided by rebaudioside A.

Figure 15:
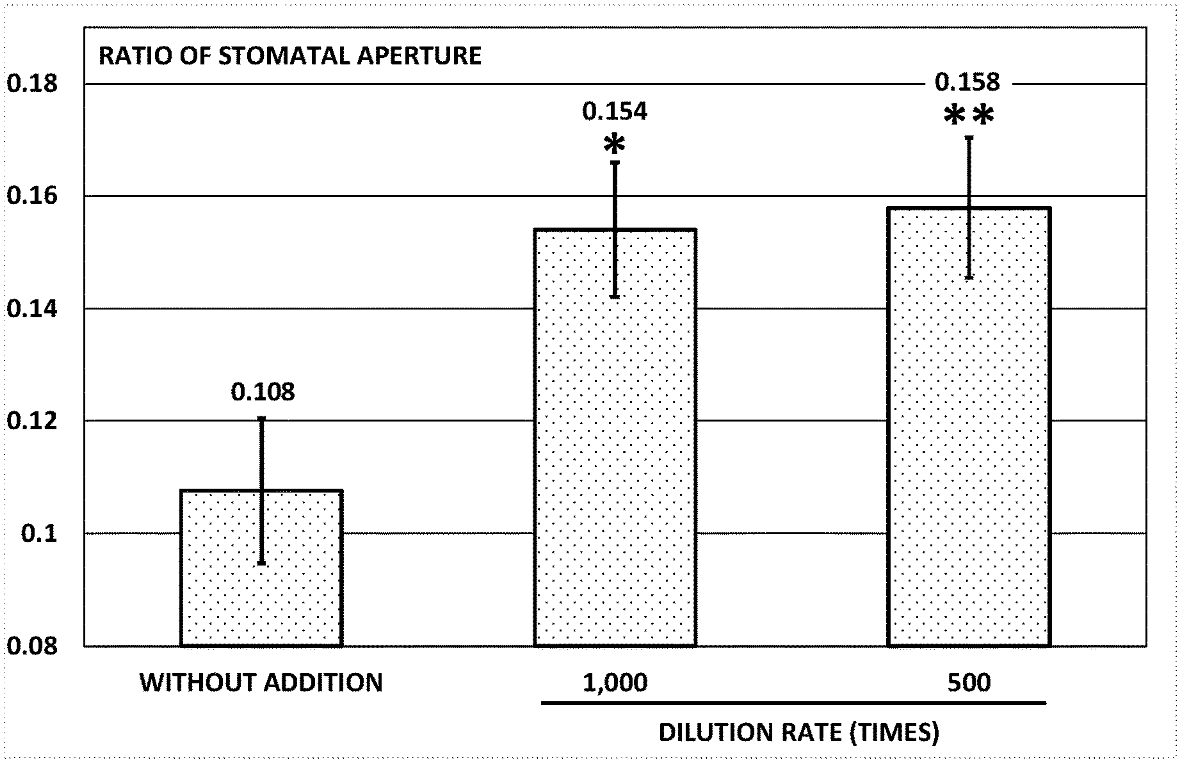

FIG. 15 is a graph showing the results of evaluation performed using tomato seedlings, on the abscisic acid-induced stomatal closure inhibitory activity provided by FARM A.

Figure 16:
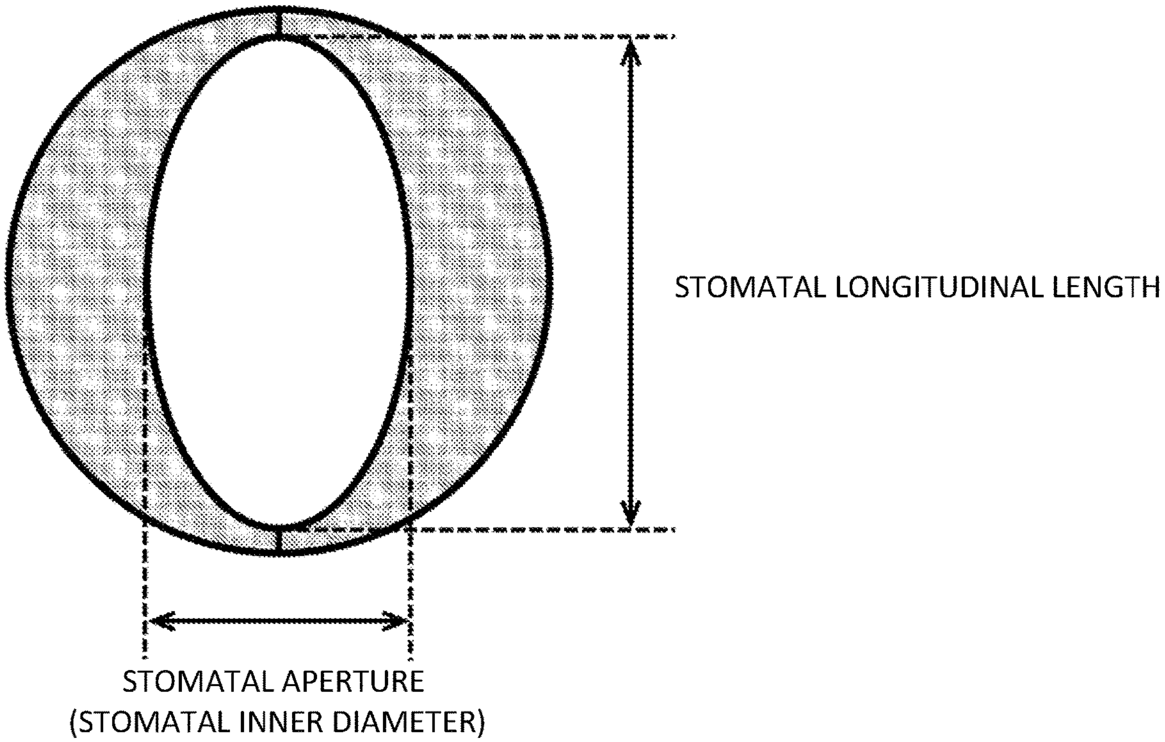

FIG. 16 is a schematic diagram of the stomatal aperture measured in Examples 1 to 15.

DESCRIPTION OF EMBODIMENTS

Stevia

Stevia (scientific name: *Stevia rebaudiana* L.) is a perennial plant in the genus *Stevia* of the family Asteraceae native to South America, which is used worldwide as a natural sweetener, a food additive, or the like. Stevia typically has a height of about 50 cm to 1 m, and the stem is covered with white fine hairs. Stevia is also named sweetleaf stevia.

As used herein, “stevia” includes the leaves, stems, and/or roots of natural stevia (hereinafter also referred to as “natural stevia”); a stevia powder obtained by making natural stevia into a powder; a component contained in natural stevia (compound isolated from stevia; hereinafter also referred to as “isolated component”); an extract from natural stevia (hereinafter also referred to as “stevia extract”); residue of such a stevia extract; and a product obtained by treating the isolated component or the stevia extract (hereinafter also referred to as “stevia-treated product or stevia derivative).

Examples of the component contained in natural stevia (isolated component) include steviol or derivatives thereof.

Of steviol compounds represented by general formula (1):

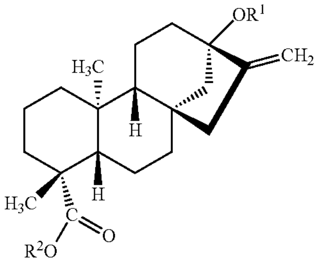

(1)

wherein $R^1$ and $R^2$ are the same or different, and each represents a hydrogen atom, a monosaccharide, a disaccharide, a trisaccharide, a tetrasaccharide, an oligosaccharide, a sugar alcohol, or an amino sugar;

steviol is a compound wherein $R^1$ and $R^2$ each represent a hydrogen atom.

Steviol derivatives are not limited as long as they are compounds derived from steviol, and examples include compounds of the steviol compounds represented by general formula (1), wherein $R^1$ and $R^2$ are the same or different, and each represent a hydrogen atom, a monosaccharide, a disaccharide, a trisaccharide, a tetrasaccharide, an oligosaccharide, a sugar alcohol, or an amino sugar (excluding the compound of general formula (1) wherein $R^1$ and $R^2$ each represent a hydrogen atom (steviol)).

Examples of monosaccharides include:

trioses such as a ketotriose (dihydroxyacetone) and an aldotriose (glyceraldehyde);

tetroses such as a ketotetrose (erythrulose) and an aldotetrose (erythrose or threose);

pentoses such as a ketopentose (ribulose or xylulose), an aldopentose (ribose, arabinose, xylose, or lyxose), and a deoxysugar (deoxyribose);

hexoses such as a ketohexose (psicose, fructose, sorbose, or tagatose), an aldohexose (allose, altrose, glucose, mannose, glucose, idose, galactose, or talose), and a deoxysugar (fucose, fuculose, or rhamnose);

heptoses such as sedoheptulose; or derivatives thereof.

Examples of disaccharides include disaccharides such as sucrose, lactose, maltose, trehalose, turanose, and cellobiose; or derivatives thereof.

Examples of trisaccharides include trisaccharides such as raffinose, melezitose, and maltotriose; or derivatives thereof.

Examples of tetrasaccharides include tetrasaccharides such as acarbose and stachyose; or derivatives thereof.

Examples of oligosaccharides include oligosaccharides such as fructooligosaccharides (FOS), galactooligosaccharides (GOS), mannan-oligosaccharides (MOS); or derivatives thereof.

Sugar alcohols are a type of sugars produced by the reduction of the carbonyl group of an aldose or a ketose, and examples include tetritols such as erythritol and threitol; pentitols such as arabitol, xylitol, and ribitol; hexitols such as iditol, galactitol, glucitol, and mannitol; heptitols such as volemitol and perseitol; maltitol; or derivatives thereof.

Amino sugars are sugars containing an amino group (amine), and examples include glucosamine, N-acetylglucosamine, N-acetylmuramic acid, galactosamine, N-acetylgalactosamine, mannosamine, N-acetylmannosamine, neuraminic acid, N-acetylneuraminic acid, daunosamine, fructosamine, hexosamine, ketosamine, muramyl dipeptide, perosamine, sialic acid; or derivatives thereof.

These monosaccharides, disaccharides, trisaccharides, tetrasaccharides, oligosaccharides, sugar alcohols, amino sugars, or derivatives thereof may be used alone or as a mixture.

A disaccharide, a trisaccharide, a tetrasaccharide, and an oligosaccharide each refer to a polymer of any two or more of the above-mentioned monosaccharides linked by glycosidic bonds.

Steviol also encompasses salts thereof.

Examples of salts of steviol include salts of steviol compounds with organic acids, inorganic acids, inorganic bases, or organic bases.

Examples of inorganic acids include hydrochloric acid, sulfuric acid, and phosphoric acid.

Examples of organic acids include carboxylic acids such as propionic acid, glycolic acid, lactic acid, hydroxybutyric acid, malic acid, maleic acid, malonic acid, salicylic acid, fumaric acid, succinic acid, adipic acid, tartaric acid, citric acid, glutaric acid, and 2- or 3-glycerophosphoric acid; organic phosphoric acids, and organic sulfonic acids.

Examples of inorganic bases include alkali metals such as sodium, potassium, and lithium; alkaline earth metals such as calcium, and ammonia.

Examples of organic bases include alkylamines (such as C1-6 alkylamines), hydroxyalkylamines (such as hydroxy C1-6 alkylamines), N-methylglucamine, benzylamine, piperidine, and pyrrolidine.

These steviol compounds may be components contained in natural stevia as mentioned above (isolated components), or may be produced by chemical synthesis.

Specific examples of the steviol compounds represented by general formula (1) include steviol, stevioside, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, dulcoside, steviolbioside, and rubusoside.

Of these steviol compounds, compounds other than steviol (compound of general formula (1) wherein $R^1$ and $R^2$ are each a hydrogen atom) may also be referred to as glycosides with the steviol backbone, i.e., "steviol glycosides". One or more of the steviol compounds may be used.

Stevioside is also called stevioside (stevioside). Rebaudioside is also called rebaudioside (rebaudiosideA). Dulcoside is also called dulcoside (dulcoside). Stebiolbioside is also called stebiolbioside (stebiolbioside). Rubusoside is also called rubusoside (rubusoside). Stebiol is also called stebiol (steviol).

The stevia extract is not limited as long as it is extracted from stevia of the family Asteraceae. Examples of the stevia extract include an extract obtained by extraction of the plant body (including the leaves, stems, and roots) of stevia at room temperature to hot water; and a purified product of the extract. Such a stevia extract may be used alone or in the form of a diluted liquid including a solution, a powder, granules, or the like. One or more of such stevia extracts may be used. Commercial stevia extracts may also be used. Examples of commercial stevia extracts include FARM A (registered trademark, manufactured by OAT Agrio Co., Ltd.) and Steviron (registered trademark) TK (manufactured by Morita Kagaku Kogyo Co., Ltd.).

The stevia-treated product (also referred to as stevia derivative) refers to a component obtained by subjecting natural stevia, a component obtained from stevia (isolated component or isolated compound), or a stevia extract to chemical treatment or enzyme treatment.

Of the above, a compound obtained by enzyme treatment of stevia (hereinafter referred to as "enzyme-treated stevia") is not limited as long as it is a treated product obtained by treating stevia or a stevia extract with an enzyme. Examples of the enzyme-treated stevia include a treated product obtained by adding glucose to the stevia extract using $\alpha$-glucosyltransferase or the like. One or more types of such enzyme-treated stevia may be used.

As used herein, "stevia" encompasses one stevia component or a stevia composition containing two or more stevia components, a stevia extract, and one or more types of enzyme-treated stevia, as well as mixtures thereof.

Preferred as the stevia are steviol, stevioside, rebaudioside A, rebaudioside B, rebaudioside C, rebaudioside D, rebaudioside E, rebaudioside F, rebaudioside M, steviolbioside, rubusoside, dulcoside, and a stevia extract; more preferred are steviol, stevioside, rebaudioside A, rebaudioside B, rebaudioside D, rebaudioside E, rebaudioside M, steviolbioside, rubusoside, dulcoside, and a stevia extract; and particularly preferred are steviol, stevioside, rebaudioside A, and a stevia extract.

The stevia used in the present invention can promote stomatal opening in a plant. Thus, at least one selected from the group consisting of stevia, stevia extracts, and enzyme-treated stevia may be used as an active ingredient in the plant stomatal opening promoting agent.

Stomatal opening in a plant is suppressed by the stomatal closure-inducing plant hormone, abscisic acid, but the plant stomatal opening promoting agent of the present invention can inhibit the activity.

Furthermore, plants are induced to close stomata under dark conditions, but the plant stomatal opening promoting agent of the present invention can counteract the inductive action. The plant stomatal opening promoting agent of the present invention has the effect of further promoting stomatal opening under bright conditions.

Plants for which the plant stomatal opening promoting agent of the present invention is used are not limited as long as they are terrestrial plants with stomata. Examples of plants for which the plant stomatal opening promoting agent of the present invention can be used include, but are not limited to:

grains, such as rice, barley, wheat, rye, oats, and maize;

legumes, such as soybeans, adzuki beans, broad beans, green peas, kidney beans, and peanuts;

fruit trees and fruits, such as apples, citruses, pears, grapes, peaches, plums, cherries, walnuts, chestnuts, almonds, bananas, and strawberries;

leaf and fruit vegetables, such as cabbage, tomatoes, spinach, broccoli, lettuce, onions, green onions, green peppers, eggplants, and peppers;

root vegetables, such as carrots, potatoes, sweet potatoes, taro, Japanese radish, lotus roots, turnips, burdock, and garlic;

crops for processing use, such as cotton, hemp, beets, hops, sugar cane, sugar beets, olives, gum, coffee, tobacco, and tea;

cucurbits, such as pumpkins, cucumbers, oriental melon, watermelons, and melons;

pasture grasses, such as orchardgrass, sorghum, timothy, clover, and alfalfa;

grasses, such as *Zoysia tenuifolia* and bentgrass;

flavoring and ornamental crops, such as lavender, rosemary, thyme, parsley, pepper, and ginger;

flowers and ornamental plants, such as chrysanthemums, roses, carnations and orchids;

garden trees, such as ginkgo, *Prunus* species, and *Aucuba japonica*; and forest trees, such as *Abies sachalinensis* species, *Picea jezoensis* species, *Pinus* species, hiba cedar, Japanese cedar, and Japanese cypress.

While the plant stomatal opening promoting agent of the present invention may contain the above-described active ingredient alone, it may also contain various additives in addition to the active ingredient, depending on the below-described dosage form, mode of application, and the like. The content of the active ingredient in the plant stomatal opening promoting agent may be determined appropriately according to the below-described dosage form, mode of application, and the like. For example, when the plant stomatal opening promoting agent of the present invention as a liquid is contacted with stomata, the content of the active ingredient is typically, for example, about 0.001 to 80,000 μM, preferably about 0.01 to 8,000 μM, and more preferably about 0.1 to 800 μM.

Dosage forms of the plant stomatal opening promoting agent of the present invention are not limited as long as they are agriculturally acceptable dosage forms, and examples include liquids, solids, powders, granules, particles, wettable powders, flowable agents, emulsions, pastes, and dispersants.

Additives are not limited as long as they are agriculturally acceptable additives, and examples include carriers, surfactants, thickeners, fillers, binding agents, vitamins, antioxidants, pH adjusters, volatilization inhibitors, and pigments.

Modes of application of the plant stomatal opening promoting agent of the present invention are not limited as long as they are known modes of using pesticides (or such modes that may be developed in the future), and examples include spraying, dropwise addition, application, and mixing or dissolving into plant growth environments (such as in soils, in water, in solid media, in liquid media, or in culture media).

EXAMPLES

The present invention will be more specifically described hereinafter, based on examples and test examples, although the technical scope of the present invention is not limited to these examples.

Materials (Raw Materials)

Steviol (manufactured by ChromaDex, Inc)

Stevioside (manufactured by Tokyo Chemical Industry Co., Ltd.)

Rebaudioside A (manufactured by Tokyo Chemical Industry Co., Ltd.)

FARM A (registered trademark, manufactured by OAT Agrio Co., Ltd.): a product obtained by mixing aboveground parts of stevia plants and water at a predetermined ratio, heating the mixture, and then subjecting the liquid phase obtained by centrifugating the mixture to vacuum concentration, followed by fermentation of the concentrate for a predetermined time; contains steviol and steviol glycosides such as stevioside and rebaudioside A (see Example 16).

Steviron (registered trademark) TK (manufactured by Morita Kagaku Kogyo Co., Ltd.): a stevia extract; a sweetener containing 80% or more of steviol glycosides.

Abscisic acid (manufactured by FUJIFILM Wako Pure Chemical Corporation or Tokyo Chemical Industry Co., Ltd.)

Stomatal aperture measurement solution (10 mM MES-KOH [pH 6.5], 50 mM KCl, and 0.1 mM $CaCl_2$, all manufactured by FUJIFILM Wako Pure Chemical Corporation)

Test solutions: solutions prepared by adding the raw materials described in Examples 1 to 15 below to the stomatal aperture measurement solution to give a predetermined final concentration were used as test solutions.

Compound solution for foliar spray treatment: an aqueous solution prepared by adding abscisic acid and steviol, stevioside, or rebaudioside A to give a predetermined final concentration, and mixing Tween (registered trademark) 80 (manufactured by Tokyo Chemical Industry Co., Ltd.) as a spreading agent to give a final concentration of 100 ppm was used as a compound solution for foliar spray treatment.

FARM A solution for foliar spray treatment: an aqueous solution prepared by adding FARM A to give a predetermined final concentration was used as a FARM A solution for foliar spray treatment.

Abscisic acid solution for foliar spray treatment: an aqueous solution prepared by adding abscisic acid to give a predetermined final concentration was used as an abscisic acid solution for foliar spray treatment.

Steviron TK solution for foliar spray treatment: an aqueous solution prepared by adding Steviron TK to give a predetermined final concentration, and mixing Tween (registered trademark) 80 (manufactured by Tokyo Chemical Industry Co., Ltd.) as a spreading agent to give a final concentration of 100 ppm was used as a Steviron TK solution for foliar spray treatment.

Example 1: Evaluation of the Stomatal Opening Promoting Activity in a Bright Place Provided by Steviol The lower epidermis of *Commelina benghalensis* L. was peeled off, immersed in the stomatal aperture measurement solution, and allowed to stand still in a dark place for 2 hours. Then, the lower epidermis of *Commelina benghalensis* L. was immersed in test solutions prepared by adding steviol to the stomatal aperture measurement solution to give 100 or 300 μM (final concentration) or in the stomatal aperture measurement solution without the addition of steviol (Comparative Example 1), and allowed to stand still in a bright place for 3 hours. The lower epidermis of *Commelina benghalensis* L. after immersion in the test solutions was photographed with a digital camera (LCD (Liquid Crystal Display), manufactured by KENIS LIMITED) attached to a microscope (Olympus BH2; objective lens SPlan 10 [manufactured by Olympus Corporation] magnification 200×). The stomatal aperture was measured with measurement software (digital microanalyzer, manufactured by Nippon Polaroid Corporation; Polaroid is the registered trademark). The stomatal aperture refers to the inner diameter of a stoma, as shown in FIG. 16. The stomatal aperture was measured for 80 or more stomata, for each addition concentration. The stomatal aperture obtained at each addition concentration was compared with the stomatal aperture obtained without the addition of steviol (0 μM, Comparative Example 1), and statistical analysis was performed by student's t-test. The results are shown in Table 1 and FIG. 1.

Figure 1:
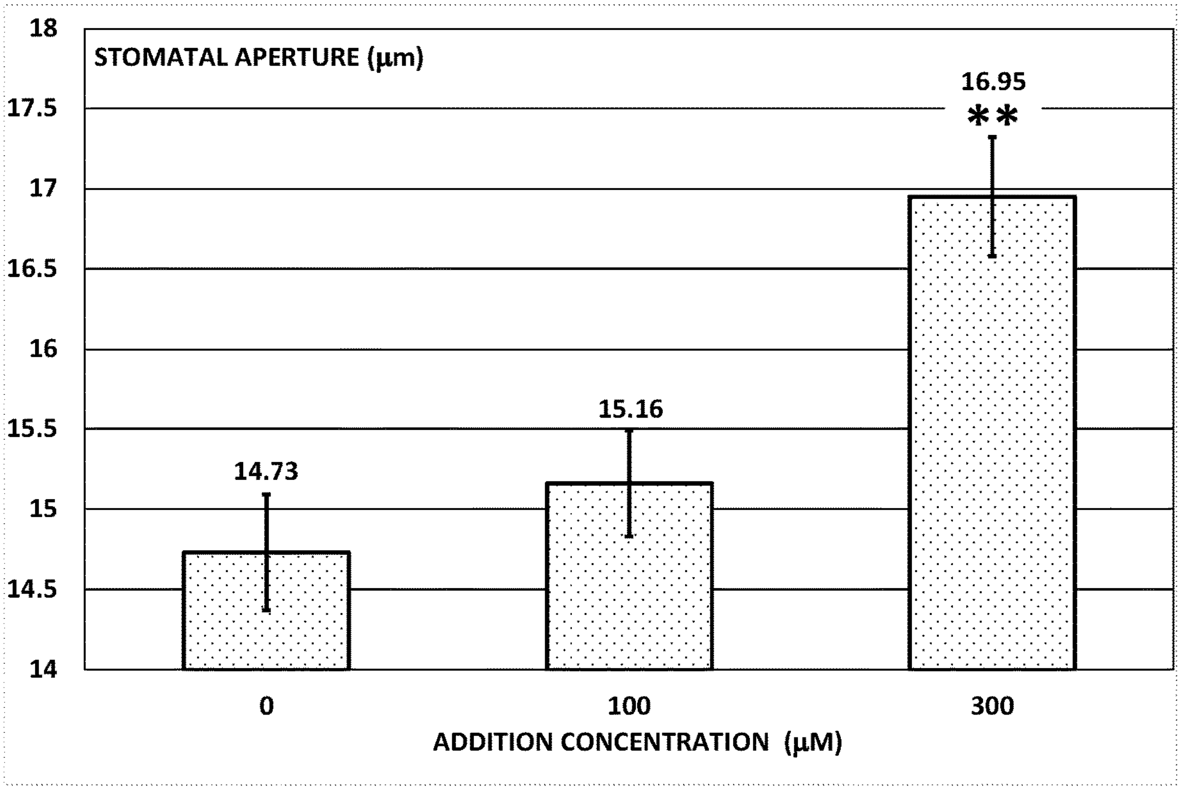
FIG. 1 is a graph showing the results of evaluation performed using the lower epidermis of *Commelina ben-*

The measurement values are shown as mean±standard deviation. In FIG. 1, and in FIGS. 2 to 15 as well, **: $P<0.01$ and *: $P<0.05$.

TABLE 1

| | Addition Concentration (μM) | Stomatal Aperture (μm) |
|---|---|---|
| Comp. Ex. 1 | 0 (without addition) | 14.73 ± 0.36 |
| Ex. 1 | 100 | 15.16 ± 0.33 |
| | 300 | 16.95 ± 0.37 |

<Results>

The addition of 100 or 300 μM of steviol showed an increase in the stomatal aperture, as compared to without the addition of steviol (0 μM: Comparative Example 1). In particular, the addition of 300 μM of steviol showed a statistically significant increase in the stomatal aperture as shown in FIG. 1, which has confirmed stomatal opening promotion in a bright place. This has revealed that steviol has a stomatal opening promoting effect.

Example 2: Evaluation of the Stomatal Opening Promoting Activity in a Bright Place Provided by FARM A The lower epidermis of *Commelina benghalensis* L. that had been peeled off was immersed in the stomatal aperture measurement solution, and allowed to stand still in a dark place for 2 hours. Then, the lower epidermis of *Commelina benghalensis* L. was immersed in test solutions prepared by adding FARM A to the stomatal aperture measurement solution to give a 500- or 250-fold dilution (final concentration) or in the stomatal aperture measurement solution without the addition of FARM A (Comparative Example 2), and allowed to stand still in a bright place for 3 hours. Then, the stomatal aperture was measured as in Example 1. The results are shown in Table 2 and FIG. 2.

TABLE 2

| | Addition Concentration (times dilution) | Stomatal Aperture (μm) |
|---|---|---|
| Comp. Ex. 2 | 0 (without addition) | 10.21 ± 0.32 |
| Ex. 2 | 500 | 12.17 ± 0.40 |
| | 250 | 12.24 ± 0.29 |

<Results>

The addition of FARM A to give a 500- or 250-fold dilution showed a statistically significant increase in the stomatal aperture as shown in FIG. 2, as compared to without the addition of FARM A (Comparative Example 2), which has confirmed stomatal opening promotion in a bright place. This has revealed that FARM A has a stomatal opening promoting effect.

Example 3: Evaluation of the Stomatal Opening Promoting Effect Provided by Steviron TK On Mar. 9, 2019, seed tubers (baron potatoes, purchased from KOMERI Co., Ltd.) were planted at a depth of 10 cm in slit pots CSM-L (manufactured by KANEYA Co., Ltd.) filled with the culture soil, Kumiai Gardening Seedling Culture Soil AISAI No. 1 (manufactured by Katakura & Co-op Agri Corporation), and after sprouting, the number of sprouts was adjusted to one. After 12:30 p.m. on April 18, plants in a similar growth state were selected, and subjected to foliar spray treatment with the Steviron TK solution for foliar spray treatment. The Steviron TK solution for foliar spray treatment was prepared by adding Steviron TK to give a 200,000-, 100,000-, 50,000-, or 25,000-fold dilution as a final concentration, and adding a spreading agent. As a control (Comparative Example 3), an aqueous solution containing the spreading agent alone was sprayed. On the following day (19th), between 11:00 a.m. and 12:30 p.m., stomatal conductance values serving as the index of stomatal opening were measured with the leaf porometer SC-1 (manufactured by METER Group, Inc.). Measurements were taken at the center of five leaflets of the second leaf counting from of a new leaf that is a fully expanded leaf of each individual plant. Of the five measured results, three values, excluding the maximum and minimum values, were collected from a total of three plants for each treatment condition, and used for subsequent analysis. Statistical analysis was performed by comparing the measured results obtained for the Steviron TK-treated plants with the results obtained for the plants treated with water containing the spreading agent only (Comparative Example 3). The results as shown in Table 3 and FIG. 3 were obtained. A higher measurement value indicates better opening of the stoma.

TABLE 3

| | Addition Concentration (times dilution) | Stomatal Conductance Value ($mmol \cdot m^{-2} \cdot s^{-1}$) |
|---|---|---|
| Comp. Ex. 3 | 0 (without addition) | 645.3 ± 43.9 |
| Ex. 3 | 200,000 | 813.7 ± 35.8 |
| | 100,000 | 845.2 ± 63.3 |
| | 50,000 | 790.0 ± 25.7 |
| | 25,000 | 781.6 ± 28.9 |

<Results>

The addition of Steviron TK at every dilution rate showed a statistically significant improvement in the stomatal conductance value as shown in FIG. 3, as compared to without the addition of Steviron TK (Comparative Example 3). This has revealed that Steviron TK has a stomatal opening promoting effect.

Example 4: Evaluation of the Stomatal Opening Promoting Activity in a Dark Place Provided by Steviol The lower epidermis of *Commelina benghalensis* L. that had been peeled off was immersed in the stomatal aperture measurement solution, and allowed to stand still in a dark place for 2 hours. Then, the lower epidermis of *Commelina benghalensis* L. was immersed in test solutions prepared by adding steviol to the stomatal aperture measurement solution to give 200 or 300 μM (final concentration) or in the stomatal aperture measurement solution without the addition of steviol (Comparative Example 4), and allowed to stand still in a dark place for 3 hours. Then, the stomatal aperture was measured as in Example 1. The results are shown in Table 4 and FIG. 4.

TABLE 4

| | Addition Concentration (μM) | Stomatal Aperture (μm) |
|---|---|---|
| Comp. Ex. 4 | 0 (without addition) | 7.08 ± 0.32 |
| Ex. 4 | 200 | 15.00 ± 0.32 |
| | 300 | 11.94 ± 0.42 |

<Results>

The addition of steviol at 200 or 300 μM showed a statistically significant increase in the stomatal aperture as shown in FIG. 4, as compared to without the addition of steviol (0 μM: Comparative Example 4), which has confirmed the stomatal opening promoting effect in a dark place. This has revealed that steviol has a stomatal opening promoting effect.

Example 5: Evaluation of the Stomatal Opening Promoting Activity in a Dark Place Provided by Stevioside The lower epidermis of *Commelina benghalensis* L. that had been peeled off was immersed in the stomatal aperture measurement solution, and allowed to stand still in a dark place for 2 hours. Then, the lower epidermis of *Commelina benghalensis* L. was immersed in test solutions prepared by adding stevioside to the stomatal aperture measurement solution to give 100, 200 or 300 μM (final concentration) or in the stomatal aperture measurement solution without the addition of stevioside (Comparative Example 5), and allowed to stand still in a dark place for 3 hours. Then, the stomatal aperture was measured as in Example 1. The results are shown in Table 5 and FIG. 5.

TABLE 5

| | Addition Concentration (μM) | Stomatal Aperture (μm) |
|---|---|---|
| Comp. Ex. 5 | 0 (without addition) | 5.45 ± 0.22 |
| Ex. 5 | 100 | 6.83 ± 0.23 |
| | 200 | 7.33 ± 0.31 |
| | 300 | 5.81 ± 0.20 |

<Results>

The addition of stevioside at 100, 200 or 300 μM showed an increase in the stomatal aperture, as compared to without the addition of stevioside (0 μM: Comparative Example 5). In particular, a stevioside addition concentration of 100 or 200 μM showed a statistically significant increase in the stomatal aperture as shown in FIG. 5, which has revealed that stevioside has a stomatal opening promoting effect in a dark place.

Example 6: Evaluation of the Stomatal Opening Promoting Activity in a Dark Place Provided by Rebaudioside A The lower epidermis of *Commelina benghalensis* L. that had been peeled off was immersed in the stomatal aperture measurement solution, and allowed to stand still in a dark place for 2 hours. Then, the lower epidermis of *Commelina benghalensis* L. was immersed in test solutions prepared by adding rebaudioside A to the stomatal aperture measurement solution to give 10, 100, 300, or 500 μM (final concentration) or in the stomatal aperture measurement solution without the addition of rebaudioside A (Comparative Example 6), and allowed to stand still in a dark place for 3 hours. Then, the stomatal aperture was measured as in Example 1. The results are shown in Table 6 and FIG. 6.

TABLE 6

| | Addition Concentration (μM) | Stomatal Aperture (μm) |
|---|---|---|
| Comp. Ex. 6 | 0 (without addition) | 7.05 ± 0.29 |
| Ex. 6 | 10 | 8.70 ± 0.39 |
| | 100 | 9.53 ± 0.45 |
| | 300 | 11.46 ± 0.55 |
| | 500 | 9.05 ± 0.40 |

<Results>

The addition of rebaudioside A at every concentration showed a statistically significant increase in the stomatal aperture as shown in FIG. 6, as compared to without the addition of rebaudioside A (0 μM: Comparative Example 6), which has confirmed stomatal opening promotion in a dark place. This has revealed that rebaudioside A has a stomatal opening promoting effect.

Example 7: Evaluation of the Stomatal Opening Promoting Activity in a Dark Place Provided by FARM A The lower epidermis of *Commelina benghalensis* L. that had been peeled off was immersed in the stomatal aperture measurement solution, and allowed to stand still in a dark place for 2 hours. Then, the lower epidermis of *Commelina benghalensis* L. was immersed in test solutions prepared by adding FARM A to the stomatal aperture measurement solution to give a 2,000-, 1,000-, or 500-fold dilution (final concentration) or in the stomatal aperture measurement solution without the addition of FARM A (Comparative Example 7), and allowed to stand still in a dark place for 3 hours. Then, the stomatal aperture was measured as in Example 1. The results are shown in Table 7 and FIG. 7.

TABLE 7

| | Addition Concentration (times dilution) | Stomatal Aperture (μm) |
|---|---|---|
| Comp. Ex. 7 | 0 (without addition) | 5.17 ± 0.32 |
| Ex. 7 | 2,000 | 11.04 ± 0.35 |
| | 1,000 | 15.59 ± 0.35 |
| | 500 | 11.63 ± 0.48 |

<Results>

The addition of FARM A at every dilution rate showed a statistically significant increase in the stomatal aperture as shown in FIG. 7, as compared to without the addition of FARM A (Comparative Example 7), which has revealed that FARM A has a stomatal opening promoting effect in a dark place.

Example 8: First Evaluation of the Abscisic Acid-Induced Stomatal Closure Inhibitory Activity Provided by Steviol The lower epidermis of *Commelina benghalensis* L. was peeled off, immersed in the stomatal aperture measurement solution, and allowed to stand still in a bright place for 3 hours. Then, the lower epidermis of *Commelina benghalensis* L. was immersed in test solutions prepared by adding 10 μM (final concentration) of abscisic acid and 400 or 600 μM of steviol to the stomatal aperture measurement solution or in the stomatal aperture measurement solution without the addition of steviol (Comparative Example 8) prepared by adding 10 μM (final concentration) of abscisic acid alone, and allowed to stand still for 2 hours. Then, the stomatal aperture was measured as in Example 1. The results are shown in Table 8 and FIG. 8.

TABLE 8

| | Addition Concentration (μM) | Stomatal Aperture (μm) |
|---|---|---|
| Comp. Ex. 8 | 0 (without addition) | 7.13 ± 0.36 |
| Ex. 8 | 400 | 10.65 ± 0.48 |
| | 600 | 13.27 ± 0.49 |

<Results>

The addition of steviol at 400 or 600 μM showed a statistically significant increase in the stomatal aperture as shown in FIG. 8, as compared to without the addition of steviol (0 μM: Comparative Example 8), which has confirmed the abscisic acid-induced stomatal closure inhibitory effect provided by steviol.

Example 9: First Evaluation of the Abscisic Acid-Induced Stomatal Closure Inhibitory Activity Provided by Stevioside The lower epidermis of *Commelina benghalensis* L. was peeled off, immersed in the stomatal aperture measurement solution, and allowed to stand still in a bright place for 3 hours. Then, the lower epidermis of *Commelina benghalensis* L. was immersed in test solutions prepared by adding 10 μM (final concentration) of abscisic acid and 300 or 800 μM (final concentration) of stevioside to the stomatal aperture measurement solution or in the stomatal aperture measurement solution without the addition of stevioside (Comparative Example 9) prepared by adding 10 μm (final concentration) of abscisic acid alone, and allowed to stand still for 2 hours. Then, the stomatal aperture was measured as in Example 1. The results are shown in Table 9 and FIG. 9.

TABLE 9

| | Addition Concentration (μM) | Stomatal Aperture (μm) |
|---|---|---|
| Comp. Ex. 9 | 0 (without addition) | 5.18 ± 0.24 |
| Ex. 9 | 300 | 7.03 ± 0.39 |
| | 800 | 6.49 ± 0.32 |

<Results>

The addition of stevioside at 300 or 800 μM showed a statistically significant increase in the stomatal aperture as shown in FIG. 9, as compared to without the addition of stevioside (0 μM: Comparative Example 9), which has confirmed the abscisic acid-induced stomatal closure inhibitory effect provided by stevioside.

Example 10: First Evaluation of the Abscisic Acid-Induced Stomatal Closure Inhibitory Activity Provided by Rebaudioside A The lower epidermis of *Commelina benghalensis* L. was peeled off, immersed in the stomatal aperture measurement solution, and allowed to stand still in a bright place for 3 hours. Then, the lower epidermis of *Commelina benghalensis* L. was immersed in test solutions prepared by adding 10 μM (final concentration) of abscisic acid and 100, 300, or 500 μM (final concentration) of rebaudioside A to the stomatal aperture measurement solution or in the stomatal aperture measurement solution without the addition of rebaudioside A (Comparative Example 10) prepared by adding 10 μm (final concentration) of abscisic acid alone, and allowed to stand still for 2 hours. Then, the stomatal aperture was measured as in Example 1. The results are shown in Table 10 and FIG. 10.

TABLE 10

| | Addition Concentration (μM) | Stomatal Aperture (μm) |
|---|---|---|
| Comp. Ex. 10 | 0 (without addition) | 6.59 ± 2.64 |
| Ex. 10 | 100 | 7.74 ± 2.90 |
| | 300 | 9.85 ± 2.57 |
| | 500 | 9.32 ± 2.69 |

<Results>

The addition of rebaudioside A at 100, 300, or 500 μM showed a statistically significant increase in the stomatal aperture as shown in FIG. 10, as compared to without the addition of rebaudioside A (0 μM: Comparative Example 10), which has confirmed the abscisic acid-induced stomatal closure inhibitory effect provided by rebaudioside A.

Example 11: First Evaluation of the Abscisic Acid-Induced Stomatal Closure Inhibitory Activity Provided by FARM A The lower epidermis of *Commelina benghalensis* L. was peeled off, immersed in the stomatal aperture measurement solution, and allowed to stand still in a bright place for 3 hours. Then, the lower epidermis of *Commelina benghalensis* L. was immersed in test solutions prepared by adding 10 μM (final concentration) of abscisic acid and FARM A to give a 500-fold dilution (final concentration) to the stomatal aperture measurement solution or in the stomatal aperture measurement solution without the addition of FARM A (Comparative Example 11) prepared by adding 10 μm (final concentration) of abscisic acid alone, and allowed to stand still for 2 hours. Then, the stomatal aperture was measured as in Example 1. The results are shown in Table 11 and FIG. 11.

TABLE 11

| | Addition Concentration (times dilution) | Stomatal Aperture (μm) |
|---|---|---|
| Comp. Ex. 11 | 0 (without addition) | 5.41 ± 0.34 |
| Ex. 11 | 500 | 9.47 ± 0.37 |

<Results>

The addition of FARM A at a 500-fold dilution showed a statistically significant increase in the stomatal aperture as shown in FIG. 11, as compared to without the addition of FARM A (Comparative Example 11), which has confirmed the abscisic acid-induced stomatal closure inhibitory effect in a bright place provided by FARM A.

Example 12: Second Evaluation of the Abscisic Acid-Induced Stomatal Closure Inhibitory Activity Provided by Steviol On Jun. 31, 2018, a seedling pot (Bee pot Y-55, manufactured by CANELON C.E) was filled with the culture soil, Kumiai Gardening Seedling Culture Soil AISAI No. 1 (manufactured by Katakura & Co-op Agri Corporation), to be level with the upper side of the pot. Two seeds of tomato (cultivar: Ponderosa) were planted in each pot, and the seedling pot was placed in a climate chamber (25° C., dark period/bright period: 11 h/13 h, bright period: 6:00 a.m. to 19:00 p.m.) at the Cultivation Research Center of OAT Agrio Co., Ltd. Water was supplied from the bottom of the pot, and plants were selected at the time of cotyledon development. At 8:30 a.m. on August 21, chemical solutions each prepared by dissolving 100 ppm of Tween (registered trademark) 80, 30 μM of abscisic acid, and 0 (Comparative Example 12), 100, 300, or 500 μM of steviol were sprayed evenly onto above-ground parts of crops grown to a plant age of about 4 in leaf number. At 11:30 a.m. and 16:00 p.m. on the same day, stomata on the underside of the top leaflet of the second leaf of crops were sampled on a cover glass with an instant adhesive (instant bond for general use AronAlpha (registered trademark) manufactured by TOAGOSEI CO., LTD.) thereon to prepare samples for stomatal observation. These samples were observed under a microscope (magnification 1,000×) to count the number of open or closed stomata in 100 or more stomata, and the ratio of open stomata was calculated according to the following equation:

$$\text{ratio (\%) of open stomata}=100\times(\text{number of open stomata})/(\text{total number of investigated stomata}) \quad \text{(Equation)}$$

The investigations were made in quadruplicate for each treatment condition. A significance test was performed by student's t-test on the ratio of open stomata obtained from the investigation of each individual plant against the ratio of open stomata obtained for the plot without the addition of steviol (0 μm: Comparative Example 12). The results are shown in Table 12 and FIG. 12.

TABLE 12

| | Addition | Ratio (%) of Open Stomata | |
|---|---|---|---|
| | Concentration (μM) | Time (11:30) | Time (16:00) |
| Comp. Ex. 12 | 0 (without addition) | 35.2 ± 5.7 | 41.1 ± 4.0 |
| Ex. 12 | 100 | 69.0 ± 5.5 | 69.3 ± 3.5 |
| | 300 | 62.7 ± 2.5 | 61.9 ± 4.6 |
| | 500 | 60.1 ± 7.5 | 62.5 ± 6.8 |

<Results>

At every addition concentration and every investigation time, the addition of steviol showed a statistically significant improvement in the ratio of open stomata as shown in FIG. 12, as compared to without the addition of steviol (0 μM: Comparative Example 12), which has confirmed the abscisic acid-induced stomatal closure inhibitory effect provided by steviol.

Example 13: Second Evaluation of the Abscisic Acid-Induced Stomatal Closure Inhibitory Activity Provided by Stevioside On Feb. 27, 2018, a seedling pot (Bee pot Y-55, manufactured by CANELON C.E) was filled with the culture soil, Kumiai Gardening Seedling Culture Soil AISAI No. 1 (manufactured by Katakura & Co-op Agri Corporation), to be level with the upper side of the pot. Two seeds of tomato (cultivar: Ponderosa) were planted in each pot, and the seedling pot was placed in a climate chamber (25° C., dark period/bright period: 11 h/13 h, bright period: 6:00 a.m. to 19:00 p.m.) at the Cultivation Research Center of OAT Agrio Co., Ltd. Water was supplied from the bottom of the pot, and plants were selected at the time of cotyledon development. At 8:30 a.m. on March 15, chemical solutions each prepared by dissolving 100 ppm of Tween (registered trademark) 80, 30 μM of abscisic acid, and 0 (Comparative Example 13), 300, or 500 μM of stevioside were sprayed evenly onto above-ground parts of crops grown to a plant age of about 3 in leaf number. At 11:30 a.m. and 16:00 p.m. on the same day, stomata on the underside of the top leaflet of the second leaf of crops were sampled on a cover glass with an instant adhesive (instant bond for general use AronAlpha (registered trademark) manufactured by TOAGOSEI CO., LTD.) thereon to prepare samples for stomatal observation. These samples were observed under a microscope (magnification 1,000×) to count the number of open or closed stomata in 100 or more stomata, and the ratio of open stomata was calculated according to the following equation:

$$\text{(Equation) ratio (\%) of open stomata} = 100\times(\text{number of open stomata})/(\text{total number of investigated stomata})$$

The investigations were made in quadruplicate for each treatment condition. A significance test was performed by student's t-test on the ratio of open stomata obtained from the investigation of each individual plant against the ratio of open stomata obtained for the plot without the addition of stevioside (0 μm: Comparative Example 13). The results are shown in Table 13 and FIG. 13.

TABLE 13

| | Addition | Ratio (%) of Open Stomata | |
|---|---|---|---|
| | Concentration (μM) | Time (11:30) | Time (16:00) |
| Comp. Ex. 13 | 0 (without addition) | 43.4 ± 3.1 | 40.9 ± 2.5 |
| Ex. 13 | 300 | 65.1 ± 6.4 | 58.0 ± 4.2 |
| | 500 | 45.7 ± 2.7 | 54.6 ± 3.8 |

<Results>

At every addition concentration and every investigation time, the addition of stevioside showed an improvement in the ratio of open stomata, as compared to without the addition of stevioside (0 μM: Comparative Example 13). In particular, the addition of stevioside at the addition concentrations and the investigation times other than the addition at 500 μM and 11:30 a.m. showed a statistically significant improvement in the ratio of open stomata as shown in FIG. 13, which has confirmed the abscisic acid-induced stomatal closure inhibitory effect provided by stevioside.

Example 14: Second Evaluation of the Abscisic Acid-Induced Stomatal Closure Inhibitory Activity Provided by Rebaudioside A On Mar. 8, 2018, a seedling pot (Bee pot Y-55, manufactured by CANELON C.E) was filled with the culture soil, Kumiai Gardening Seedling Culture Soil AISAI No. 1 (manufactured by Katakura & Co-op Agri Corporation), to be level with the upper side of the pot. Two seeds of tomato (cultivar: Ponderosa) were planted in each pot, and the seedling pot was placed in a climate chamber (25° C., dark period/bright period: 11 h/13 h, bright period: 6:00 a.m. to 19:00 p.m.) at the Cultivation Research Center of OAT Agrio Co., Ltd. Water was supplied from the bottom of the pot, and plants were selected at the time of cotyledon development.

At 8:30 a.m. on March 27, chemical solutions each prepared by dissolving 100 ppm of Tween (registered trademark) 80, 30 μM of abscisic acid, and 0 (Comparative Example 14), 100, 300, or 500 μM of rebaudioside A were sprayed evenly onto above-ground parts of crops grown to a plant age of about 3 in leaf number. At 11:30 a.m. and 16:30 p.m. on the same day, stomata on the underside of the top leaflet of the second leaf of crops were sampled on a cover glass with an instant adhesive (instant bond for general use AronAlpha (registered trademark) manufactured by TOAGOSEI CO., LTD.) thereon to prepare samples for stomatal observation. These samples were observed under a microscope (magnification 1,000×) to count the number of open or closed stomata in 100 or more stomata, and the ratio of open stomata was calculated according to the following equation:

(Equation) ratio (%) of open stomata =

100×(number of open stomata)/(total number of investigated stomata)

The investigations were made in quadruplicate for each treatment condition. A significance test was performed by student's t-test on the ratio of open stomata obtained from the investigation of each individual plant against the ratio of open stomata obtained for the plot without the addition of rebaudioside A (0 μm: Comparative Example 14). The results are shown in Table 14 and FIG. 14.

TABLE 14

| | Addition Concentration (μM) | Ratio (%) of Open Stomata Time (11:30) | Ratio (%) of Open Stomata Time (16:30) |
|---|---|---|---|
| Com. Ex. 14 | 0 (without addition) | 40.2 ± 4.5 | 35.4 ± 2.5 |
| Ex. 14 | 100 | 56.6 ± 5.8 | 50.0 ± 3.2 |
| | 300 | 58.6 ± 4.6 | 51.2 ± 2.1 |
| | 500 | 56.5 ± 3.8 | 54.0 ± 6.6 |

<Results>

At every addition concentration and every investigation time, the addition of rebaudioside A showed an improvement in the ratio of open stomata, as compared to without the addition of rebaudioside A (0 μM: Comparative Example 10). In particular, the addition of rebaudioside A at concentrations of 300 and 500 μM showed a statistically significant improvement in the ratio of open stomata as shown in FIG. 14, which has confirmed the abscisic acid-induced stomatal closure inhibition provided by rebaudioside A.

Example 15: Second Evaluation of the Abscisic Acid-Induced Stomatal Closure Inhibitory Activity Provided by FARM A On Oct. 18, 2017, a seedling pot (Bee pot Y-55, manufactured by CANELON C.E) was filled with the culture soil, Kumiai Gardening Seedling Culture Soil AISAI No. 1 (manufactured by Katakura & Co-op Agri Corporation), to be level with the upper side of the pot. Two seeds of tomato (cultivar: Ponderosa) were planted in each pot, and the seedling pot was placed in a climate chamber (25° C., dark period/bright period: 11 h/13 h, bright period: 6:00 a.m. to 19:00 p.m.) at the Cultivation Research Center of OAT Agrio Co., Ltd. Water was supplied from the bottom of the pot, and plants were selected at the time of cotyledon development. At 9:00 a.m. on November 7, chemical solutions each prepared by dissolving 100 ppm of Tween (registered trademark) 80, 10 μM of abscisic acid, and FARM A to give a 1,000- or 500-fold dilution or without FARM A (Comparative Example 15) were sprayed evenly onto above-ground parts of crops grown to a plant age of about 3 in leaf number. At 11:30 a.m. on the following day, stomata on the underside of the top leaflet of the second leaf of crops were sampled on a cover glass with an instant adhesive (instant bond for general use AronAlpha (registered trademark) manufactured by TOAGOSEI CO., LTD.) thereon to prepare samples for stomatal observation. These samples were observed under a microscope (magnification 1,000×), and eight stomata in the same field of view were measured for stomatal aperture and stomatal longitudinal length (see FIG. 16). Then, the stomatal aperture was calculated according to the following equation, and the average value of these values was calculated. The investigations were made in quadruplicate for each condition. A significance test was performed by student's t-test on the obtained average values. The results are shown in Table 15 and FIG. 15.

(Equation) ratio of stomatal aperture = stomatal aperture (μm)/stomatal longitudinal length (μm)

TABLE 15

| | Addition Concentration (times dilution) | Ratio of Stomatal Aperture |
|---|---|---|
| Comp. Ex. 15 | 0 (without addition) | 0.108 ± 0.013 |
| Ex. 15 | 1,000 | 0.154 ± 0.012 |
| | 500 | 0.158 ± 0.012 |

<Results>

At every dilution rate, the addition of FARM A showed a statistically significant improvement in the ratio of stomatal aperture as shown in FIG. 15, as compared to without the addition of FARM A (Comparative Example 15), which has confirmed the abscisic acid-induced stomatal closure inhibitory effect in a bright place provided by FARM A.

Example 16: Analysis of Steviol and Steviol Glycosides Contents in FARM A

Steviol, stevioside, and rebaudioside A contents in FARM A were analyzed by high-performance liquid chromatography (HPLC). The analytical instrument was a liquid chromatographic apparatus (manufactured by JASCO Corporation) made up of the solvent low-pressure gradient pump model PU-2089, the intelligent autosampler model AS-2051, the PDA detector model MD-2018, and the column oven CO-2067. The analytical column was L-column 2 ODS 5 μm (size: 4.6×250 mm, manufactured by Chemicals Evaluation and Research Institute, Japan). The mobile phase for steviol was a 40:60 mixed solution of water containing 0.1% phosphoric acid (manufactured by Wako Pure Chemical Industries, Ltd.) and acetonitrile, and the mobile phase for stevioside and rebaudioside A was a 70:30 mixed solution of water containing 0.1% phosphoric acid and acetonitrile. The flow rate was set to 1 mL/min, the column temperature was set to 40° C. and the detection was set to a UV absorption spectrum at 210 nm, and elution was performed to detect and quantify the peak derived from each compound. A 10-fold dilution of FARM A was prepared, filtered and used as an analytical sample. The obtained peak area of the absorption spectrum was fitted to the approximation in the calibration curve prepared with the standard, and the concentration in the sample was calculated. The results are shown in Table 16 below.

TABLE 16

| | Compound Name | Concentration (mg/g) in Product |
|---|---|---|
| Compound (1) | Steviol | 0.04 |
| Compound (2) | Stevioside | 4.05 |
| Compound (3) | Rebaudioside A | 4.18 |

<Results>

The results have confirmed that FARM A contains steviol and steviol glycosides.

The invention claimed is:

1. A method of promoting stomatal opening in a plant, comprising:

applying a stevia composition on a plant or in a soil or a culture medium in which the plant is grown, allowing the plant to stand still in a bright place, and measuring stomatal conductance values of a leaf of the plant;

wherein the plant is a root vegetable or a fruit vegetable wherein the stevia composition comprises a stevia extract, and wherein the stevia extract comprises 80% or more of steviol glycosides, and further comprises 20% or less of other components besides the steviol glycosides, wherein the stevia extract is a powder, and the stevia composition is an aqueous solution, and wherein the stevia composition has a 200,000-, 100,000-, 50,000-, or 25,000-fold dilution of the stevia extract as a final concentration, and wherein the measured stomatal conductance values range from 781.6 (±28.9) to 845.2 (±63.3) $mmol \cdot m^{-2} \cdot s^{-1}$ and are higher than those of an untreated plant.

2. The method of promoting stomatal opening in a plant according to claim 1, wherein the stevia composition further comprises a spreading agent.

* * * * *